(12) United States Patent
Dillon et al.

(10) Patent No.: US 10,363,342 B2
(45) Date of Patent: Jul. 30, 2019

(54) ANTI-INFLAMMATORY CANNULA

(71) Applicant: Insulet Corporation, Acton, MA (US)

(72) Inventors: Bryan Dillon, Jefferson, MA (US); Bryan Choate, Salem, MA (US)

(73) Assignee: INSULET CORPORATION, Acton, MA (US)

( * ) Notice: Subject to any disclaimer, the term of this patent is extended or adjusted under 35 U.S.C. 154(b) by 3 days.

(21) Appl. No.: 15/419,369

(22) Filed: Jan. 30, 2017

(65) Prior Publication Data
US 2017/0224877 A1    Aug. 10, 2017

Related U.S. Application Data

(60) Provisional application No. 62/291,185, filed on Feb. 4, 2016.

(51) Int. Cl.
| | |
|---|---|
| A61L 29/16 | (2006.01) |
| A61M 5/158 | (2006.01) |
| A61M 5/142 | (2006.01) |
| A61L 29/06 | (2006.01) |
| A61L 29/08 | (2006.01) |
| A61L 33/06 | (2006.01) |

(52) U.S. Cl.
CPC .............. *A61L 29/16* (2013.01); *A61L 29/06* (2013.01); *A61L 29/085* (2013.01); *A61L 33/068* (2013.01); *A61M 5/14248* (2013.01); *A61M 5/158* (2013.01); *A61L 2300/42* (2013.01); *A61L 2420/08* (2013.01); *A61M 2005/1586* (2013.01)

(58) Field of Classification Search
CPC .......... A61M 2005/1586; A61M 5/158; A61M 2205/0238; A61L 29/08
See application file for complete search history.

(56) References Cited

U.S. PATENT DOCUMENTS

| | | |
|---|---|---|
| 303,013 A | 8/1884 | Horton |
| 3,631,847 A | 1/1972 | Hobbs |
| 3,812,843 A | 5/1974 | Wootten |
| 3,841,328 A | 10/1974 | Jensen |
| 4,559,033 A | 12/1985 | Stephen et al. |
| 4,743,243 A | 5/1988 | Vaillancourt |
| 4,755,173 A | 7/1988 | Konopka et al. |

(Continued)

FOREIGN PATENT DOCUMENTS

| | | |
|---|---|---|
| EP | 0341049 A2 | 11/1989 |
| EP | 0496305 A2 | 7/1992 |

(Continued)

OTHER PUBLICATIONS

US 5,954,699 A, 09/1999, Jost et al. (withdrawn)

(Continued)

*Primary Examiner* — Nathan R Price
*Assistant Examiner* — Tasnim Mehjabin Ahmed

(57) ABSTRACT

Various embodiments of the present invention include a cannula coated or compounded with a material to extend the wear time for a patient by reducing inflammation and therefore increasing the time that the cannula may remain inserted, thereby increasing the effectiveness of the drug delivered using the cannula. The material may include a hydrophilic material, an anti-microbial material, an anti-inflammatory material, anti-thrombogenic material, or a combination of any of these materials.

17 Claims, 2 Drawing Sheets

200A

200B

(56) References Cited

U.S. PATENT DOCUMENTS

| | | | |
|---|---|---|---|
| 4,781,688 A | 11/1988 | Thoma et al. | |
| 4,781,693 A | 11/1988 | Martinez et al. | |
| 4,886,499 A | 12/1989 | Cirelli et al. | |
| 4,994,047 A * | 2/1991 | Walker | A61L 29/06 600/581 |
| 5,109,850 A | 5/1992 | Blanco et al. | |
| 5,125,415 A | 6/1992 | Bell | |
| 5,176,662 A | 1/1993 | Bartholomew et al. | |
| 5,178,609 A | 1/1993 | Ishikawa | |
| 5,257,980 A | 11/1993 | Van Antwerp et al. | |
| 5,505,709 A | 4/1996 | Funderburk et al. | |
| 5,545,152 A | 8/1996 | Funderburk et al. | |
| 5,584,813 A | 12/1996 | Livingston et al. | |
| 5,613,956 A | 3/1997 | Patterson et al. | |
| 5,643,213 A | 7/1997 | McPhee | |
| 5,685,859 A | 11/1997 | Komerup | |
| 5,693,018 A | 12/1997 | Kriesel et al. | |
| 5,716,343 A | 2/1998 | Kriesel et al. | |
| 5,741,228 A | 4/1998 | Lambrecht et al. | |
| 5,755,682 A | 5/1998 | Knudson et al. | |
| 5,800,405 A | 9/1998 | McPhee | |
| 5,800,420 A | 9/1998 | Gross et al. | |
| 5,848,991 A | 12/1998 | Gross et al. | |
| 5,851,197 A | 12/1998 | Marano et al. | |
| 5,858,005 A | 1/1999 | Kriesel | |
| 5,865,806 A | 2/1999 | Howell | |
| 5,871,470 A | 2/1999 | McWha | |
| 5,931,814 A | 8/1999 | Alex et al. | |
| 5,993,423 A | 11/1999 | Choi | |
| 5,997,501 A | 12/1999 | Gross et al. | |
| 6,050,978 A | 4/2000 | Orr et al. | |
| 6,071,292 A | 6/2000 | Makower et al. | |
| 6,090,092 A | 7/2000 | Fowles et al. | |
| 6,126,637 A | 10/2000 | Kriesel et al. | |
| 6,200,338 B1 * | 3/2001 | Solomon | A61L 27/18 428/36.9 |
| 6,244,776 B1 | 6/2001 | Wiley | |
| 6,309,370 B1 | 10/2001 | Haim et al. | |
| 6,475,196 B1 * | 11/2002 | Vachon | A61L 29/085 604/132 |
| 6,569,125 B2 | 5/2003 | Jepson et al. | |
| 6,572,542 B1 | 6/2003 | Houben et al. | |
| 6,699,221 B2 | 3/2004 | Vaillancourt | |
| 6,740,059 B2 | 5/2004 | Flaherty | |
| 7,008,404 B2 | 3/2006 | Nakajima | |
| 7,025,744 B2 | 4/2006 | Utterberg et al. | |
| 7,128,727 B2 | 10/2006 | Flaherty et al. | |
| 7,303,549 B2 | 12/2007 | Flaherty et al. | |
| 7,918,825 B2 | 4/2011 | O'Connor et al. | |
| 2001/0053895 A1 | 12/2001 | Vaillancourt | |
| 2002/0010423 A1 | 1/2002 | Gross et al. | |
| 2002/0123740 A1 | 9/2002 | Flaherty et al. | |
| 2003/0163097 A1 | 8/2003 | Fleury et al. | |
| 2004/0116847 A1 | 6/2004 | Wall | |
| 2005/0020980 A1 | 1/2005 | Inoue et al. | |
| 2005/0203461 A1 | 9/2005 | Flaherty et al. | |
| 2006/0134323 A1 * | 6/2006 | O'Brien | B41M 1/02 427/162 |
| 2006/0204535 A1 | 9/2006 | Johnson | |
| 2006/0253085 A1 | 11/2006 | Geismar et al. | |
| 2007/0129690 A1 * | 6/2007 | Rosenblatt | A61L 29/16 604/265 |
| 2007/0282269 A1 | 12/2007 | Carter et al. | |
| 2008/0065050 A1 | 3/2008 | Sparks et al. | |
| 2008/0078400 A1 * | 4/2008 | Martens | A61L 29/085 128/207.15 |
| 2008/0132880 A1 | 6/2008 | Buchman | |
| 2008/0287906 A1 | 11/2008 | Burkholz et al. | |
| 2009/0069787 A1 | 3/2009 | Estes et al. | |
| 2009/0099521 A1 | 4/2009 | Gravesen et al. | |
| 2010/0152658 A1 | 6/2010 | Hanson et al. | |
| 2011/0054390 A1 | 3/2011 | Searle et al. | |
| 2011/0054399 A1 | 3/2011 | Chong et al. | |
| 2011/0144586 A1 | 6/2011 | Michaud et al. | |
| 2011/0230833 A1 | 9/2011 | Landman et al. | |
| 2011/0251509 A1 * | 10/2011 | Beyhan | A61M 16/0463 600/529 |
| 2012/0010594 A1 | 1/2012 | Holt et al. | |
| 2012/0078161 A1 | 3/2012 | Masterson et al. | |
| 2013/0060233 A1 | 3/2013 | O'Connor et al. | |
| 2013/0178791 A1 | 7/2013 | Javitt | |
| 2014/0074033 A1 | 3/2014 | Sonderegger et al. | |
| 2014/0128839 A1 | 5/2014 | Dilanni et al. | |
| 2014/0316379 A1 | 10/2014 | Sonderegger et al. | |
| 2016/0015891 A1 | 1/2016 | Papiorek | |
| 2016/0038689 A1 | 2/2016 | Lee et al. | |

FOREIGN PATENT DOCUMENTS

| | | |
|---|---|---|
| EP | 2397181 A1 | 12/2011 |
| EP | 2830499 A1 | 2/2015 |
| WO | 9800193 A1 | 1/1998 |
| WO | 9956803 A1 | 11/1999 |
| WO | 0030705 A1 | 6/2000 |
| WO | 0172354 A2 | 10/2001 |
| WO | 2002015954 A1 | 2/2002 |
| WO | 2006053007 A2 | 5/2006 |
| WO | 2007064835 A2 | 6/2007 |
| WO | 2008024810 A2 | 2/2008 |
| WO | 2008133702 A1 | 11/2008 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2013078200 A1 | 5/2013 |
| WO | 20130149186 A1 | 10/2013 |
| WO | 2013182321 A1 | 12/2013 |
| WO | 2014194183 A2 | 12/2014 |
| WO | 2015061493 A1 | 4/2015 |
| WO | 2015081337 A2 | 6/2015 |
| WO | 2016141082 A1 | 9/2016 |
| WO | 2017205816 A1 | 11/2017 |

OTHER PUBLICATIONS

International Search Report and Written Opinion for Application No. PCT/US2017/015601, dated May 16, 2017, 12 pages.

International Search Report and Written Opinion for Application No. PCT/US2018/018901, dated Aug. 6, 2018, 12 pages.

International Search Report and Written Opinion for Application No. PCT/US2018/052464, dated Jan. 4, 2019, 13 pages.

* cited by examiner

100A

100B

200A

200B

ANTI-INFLAMMATORY CANNULA

CROSS-REFERENCE TO RELATED APPLICATIONS

This application claims priority to U.S. Provisional Patent Application No. 62/291,185, filed Feb. 4, 2016, the entirety of which is hereby incorporated by reference.

TECHNICAL FIELD

Embodiments of the present invention relate generally to medication delivery and, more particularly, to systems and methods for long-term cannula usage.

BACKGROUND

A cannula is a thin tube that can be inserted into a patient's vasculature, body cavity or tissue to administer drugs, drain fluids, or insert a surgical instrument. A needle may be used to facilitate the percutaneous delivery of a cannula through the patient's skin so that when placed into its working configuration, the proximal end of the cannula remains outside of the patient's body while the distal end is placed within the intended body lumen, cavity or tissue.

Cannulas may be used for short-term or long-term treatment or therapy. For example, the cannula may remain in place for an extended time period for the long-term delivery of drugs for patients undergoing chemotherapy, for insulin delivery or for the delivery of other fluids via intravenous infusion, drug pumps, a syringe, or the like. Regardless, the use of cannulas may result in inflammation, infection or thrombus formation due to factors such as the presence or introduction of bacteria at the cannula insertion site and unintended blood flow into the cannula. Such inflammation, infection or thrombus formation may cause discomfort or harm to the patient and, in the case of long term drug therapy, may impact therapy effectiveness due to the physiological changes caused by the inflammation at the insertion site.

DETAILED DESCRIPTION

Various embodiments of the present invention include a cannula coated or compounded with a material to extend the wear time for a patient by reducing inflammation and increasing the time that the cannula may remain inserted, thereby improving the effectiveness of the drug delivered using the cannula or increasing the effectiveness of the use of the cannula. The material may include a hydrophilic material, an anti-microbial material, an anti-inflammatory material, anti-thrombogenic material, or a combination of any of these materials.

The cannula may be made of any suitable material, including polymeric, metallic and composite materials. In some embodiments, the cannula is made using an elastomeric polymer material such as fluoropolymer, polyurethane, or silicone. In these embodiments, the cannula may be soft and/or flexible. In other embodiments, the cannula is made from a rigid material such as metal or rigid plastic, such as polyvinyl chloride. The cannula may be manufactured by extruding or molding the material into a tube or other shape (or by any other means known in the art).

Figure 1A:
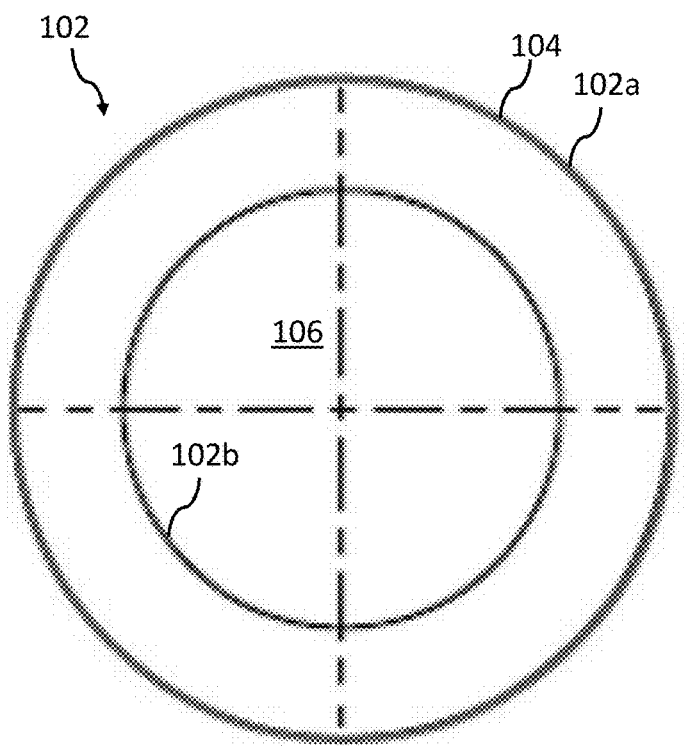
FIG. 1A illustrates a first view of a first embodiment of a cannula.
Figure 1B:
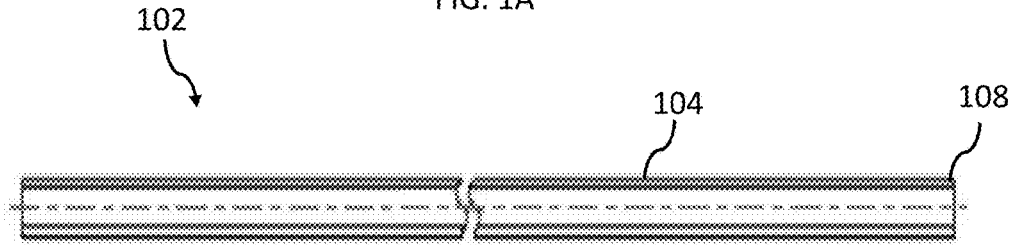
FIG. 1B illustrates a second view of the first embodiment of the cannula.

FIGS. 1A and 1B illustrate axial 100A and longitudinal 100B cross-sectional views, respectively, of a cannula 102 in accordance with embodiments of the present invention. The cannula 102 generally comprises an extended member having an open lumen 106 therein, and terminating at a distal end 108. Although the lumen 106 is illustrated as being circular in cross-sectional shape, any suitable cross-sectional shape may be used in the present invention, including ovular and rectangular. The cannula 102 can be configured to be inserted through a patient's skin by delivery with a needle or the like, such that the distal end 108 is implanted into the intended vasculature, tissue or body cavity.

In various embodiments, the cannula 102 can include a first material, such as a polymer or metal, and can be coated with a coating 104. As shown in FIGS. 1A and 1B, the coating 104 can at least partially coat the outer or exterior surface 102a of cannula 102. In other embodiments, the coating 104 can at least partially coat the inner surface 102b of the cannula 102, in addition to or instead of coating the exterior surface 102a of cannula 102.

The coating 104 can include a second material that may be a hydrophilic material, an anti-microbial material, an anti-inflammatory material, an anti-thrombogenic material, or any combination thereof. Examples of coating material types include polymers that provide desired surface characteristics, polymers that include drugs admixed therein, drugs that can be directly applied to the cannula 102 without the need for a polymer, metal-polymer combinations, and metallic materials. Such materials include, for example, heparin, silver and its alloys, rifampicin, sparfloxacin, triclosan, benalkonium chloride, tridodecylmethylammonium chloride, cefazolin, chitosan, dexamethasone sodium phosphate, polyvinylpyrolidone (PVP), polyurethanes, fluoropolymers, silicone, polyacrylic acid (PAA), polyethylene oxide (PEO), polysaccharides, fluorine-acryl-styrene-urethane-silicone (FASUS), and other suitable materials. In various embodiments, the coating 104 can comprise polyurethane and/or fluorinated ethylene propylene. In various other embodiments, the coating 104 comprises fluorinated ethylene propylene or fluorinated ethylene-propylene copolymer applied to the inner surface 102b of cannula 102 and a polyether block amide applied to the exterior surface 102a of cannula 102.

The coating 104 may be deposited on either or both of the exterior surface 102a and inner surface 102b of the cannula 102 by vapor deposition, liquid application, dip coating, spray coating or any other suitable means. In other embodiments, the coating 104 can be manufactured together with the cannula 102 during a co-extrusion process. If the coating 104 includes more than one of the hydrophilic material, anti-microbial material, and/or anti-inflammatory material, these components may be mixed homogenously, disposed in discrete layers or regions of the coating 104, or be disposed in concentration gradients throughout the coating 104. In certain embodiments, the coating 104 can include multiple layers of the same or different materials.

The thickness of the coating 104 can depend upon the specific clinical application and the material used in the coating. As non-limiting examples, the coating 104 can be formed up to 500 microns in thickness, preferably up to 100 microns, and more preferably up to 50 microns. In some embodiments, the coating 104 can be applied along the entire length of either or both of the inner and exterior surfaces of cannula 102, while in other embodiments, the coating 104 can be applied along only a portion of the length of the cannula 102 (e.g., a distal segment of the cannula 102 terminating at the distal end 108). It should also be appreciated that the coating 104 may be applied to the entire perimeter of either or both of the inner and exterior surfaces of cannula 102, or to only a portion of the perimeter.

In various embodiments, the coating 104 can be applied to the exterior surface 102a of a cannula 102 that is part of a wearable drug-delivery pump, such as an OmniPod® (Insulet Corporation, Billerica, Mass., USA). Aspects of such pumps may be described in U.S. Pat. Nos. 7,030,549; 7,144,384; 7,137,964; 6,960,192; 6,740,059; 6,699,218 and 6,656,159, each of which is incorporated herein by reference. In various embodiments, as shown and described in the aforementioned referenced U.S. patents, a cannula (e.g., the cannula 102 can extend from an insulin pump that is adhered to the patient's skin with an adhesive material located on a pump housing. Insulin is delivered at programmed infusion rates over prolonged time periods (e.g., five to seven days) from a chamber within the housing that holds the insulin in the pump through the cannula 102 that extends from the pump and through the patient's skin. In this embodiment, the cannula 102 is at least partially coated on its exterior surface 102a with a coating 104 that comprises an anti-inflammatory agent. The cannula 102 is in fluid connection to the chamber, and the distal end of the cannula 102 extends into the patient (see, e.g., U.S. Pat. No. 7,137,964, FIGS. 1-6, col. 5, line 53 col. 11, line 62).

Figure 2A:
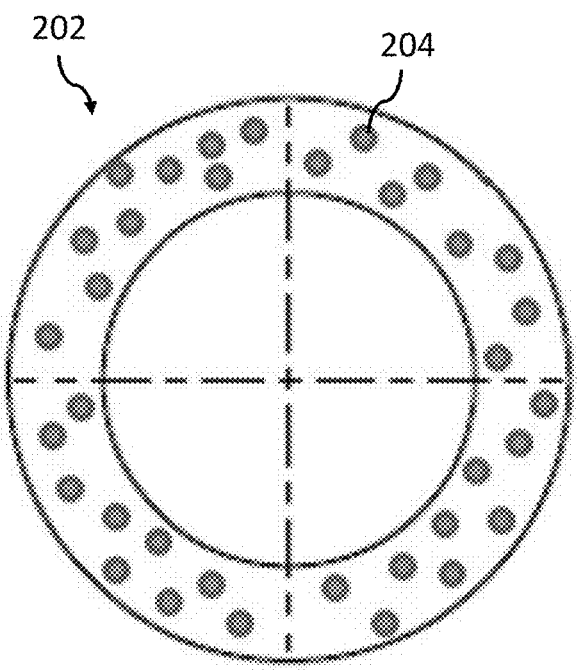
FIG. 2A illustrates a first view of a second embodiment of a cannula.
Figure 2B:
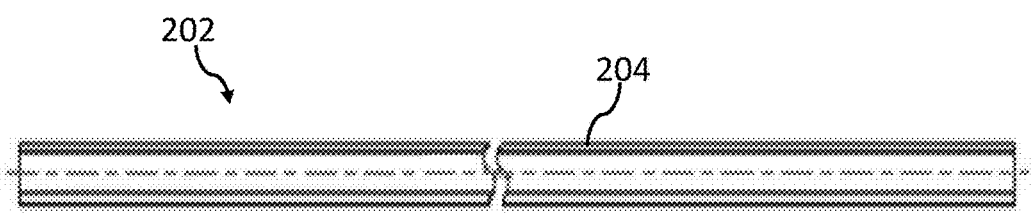
FIG. 2B illustrates a second view of the second embodiment of the cannula.

FIGS. 2A and 2B illustrate axial 200A and longitudinal 200B cross-sectional views, respectively, of a cannula 202 in accordance with other embodiments of the present invention. In these embodiments, the cannula 202 can be made of a first material, and a second material can be mixed/compounded with the first material. The second material can be the hydrophilic material, anti-microbial material, anti-inflammatory material and/or anti-thombogenic material, or a combination thereof, as described for embodiments with coating 104. As illustrated, the second material may be disposed in relatively large, discrete regions 204 in the cannula 202. In other embodiments, however, the second material can be disposed in smaller regions in the cannula 202. Any degree of mixing/compounding is within the scope of the present invention, including homogeneous dispersions and preferential placement within cannula 202.

Overall, various embodiments provide a cannula that can be made of one or more materials. The cannula can include a coating positioned over all or a portion of an outer and/or inner surface of the cannula. The coating can be made from one or more materials. The same coating can be applied to the inner or outer surface or different coatings can be applied to the inner and outer surfaces of the cannula. One or more materials can be used as a coasting for either the inner or the outer surfaces. For example, a first portion of the cannula can be coasted with a first material and a second portion of the cannula can be coated with a second material. The first and second portions can overlap. Any of the materials described herein can be used for the coating or covering for the cannula (or otherwise applied to a surface of the cannula). Any of the materials described herein can be used to form the cannula body. In various other embodiments, the cannula can be formed from two or more materials with one of the materials comprising a hydrophilic material, an anti-microbial material, an anti-inflammatory material and/or an anti-thombogenic material, or any combination thereof. For example, a first material can be impregnated or combined with one or more second materials to form the cannula, with the second materials selected from a hydrophilic material, an anti-microbial material, an anti-inflammatory material and/or an anti-thombogenic material, or any combination thereof. One or more coatings of one or more different materials can then be further applied to any surface of such a cannula.

What is claimed is:

1. A wearable fluid delivery device, comprising:
    a chamber containing a fluid to be delivered into a body of a patient; and
    a cannula in fluid connection with the chamber, the cannula comprising an exterior surface, an inner surface, a lumen and a distal end extending into the patient, wherein the cannula comprises a first material and a second material mixed with the first material, the second material disposed in discrete regions of the cannula, the second material comprising at least one of a hydrophilic material, an anti-microbial material, an anti-inflammatory material, and an anti-thombogenic material, wherein a first coating at least partially covers the exterior surface of the cannula, the first coating comprising an anti-inflammatory agent, wherein a second coating at least partially covers the interior surface of the cannula, the second coating comprising at least one of the hydrophilic material, the anti-microbial material, the anti-inflammatory material, and the anti-thombogenic material,
    wherein the second coating covers less than an entire length of the inner surface of the cannula,
    wherein the first coating covers less than an entire length of the exterior surface of the cannula,
    wherein the second coating coats less than an entire perimeter of the inner surface of the cannula,
    wherein the first coating coats less than an entire perimeter of the exterior surface of the cannula,
    wherein a third coating at least partially covers the exterior surface of the cannula, the third coating comprising at least one of the hydrophilic material, the anti-microbial material, the anti-inflammatory material, and the anti-thombogenic material, wherein the first and second coatings comprise different materials,
    wherein the third coating is disposed in a concentration gradient throughout the first coating.

2. The wearable fluid delivery device of claim 1, wherein the first material of the cannula comprises a polymeric material.

3. The wearable fluid delivery device of claim 1, the first coating having a thickness of up to 500 microns.

4. The wearable fluid delivery device of claim 1, the first coating having a thickness of up to 50 microns.

5. The wearable fluid delivery device of claim 1, wherein the first coating comprises a material selected from the group consisting of heparin, silver and its alloys, rifampicin, sparfloxacin, triclosan, benalkonium chloride, tridodecylmethylammonium chloride, cefazolin, chitosan, dexamethasone sodium phosphate, polyvinylpyrolidone (PVP), polyurethanes, fluoropolymers, silicone, polyacrylic acid (PAA), polyethylene oxide (PEO), polysaccharides, polyether block amides, and fluorine-acryl-styrene-urethane-silicone (FA-SUS).

6. The wearable fluid delivery device of claim 5, wherein the first material of the cannula comprises polyurethane.

7. The wearable fluid delivery device of claim 5, wherein the first coating comprises a polyether block amide.

8. The wearable fluid delivery device of claim 1, wherein said second coating comprises an anti-thrombogenic material.

9. The wearable fluid delivery device of claim 8, wherein said second coating comprises a fluorinated ethylene propylene.

10. The wearable fluid delivery device of claim 1, wherein the cannula comprises a single unitary body.

11. The wearable fluid delivery device of claim 1, wherein a fourth coating at least partially covers the inner surface of the cannula, the fourth coating comprising at least one of a hydrophilic material, an anti-microbial material, an anti-inflammatory material, and an anti-thombogenic material, the second and fourth coatings comprising different materials.

12. The wearable fluid delivery device of claim 11, wherein the second and fourth coatings are mixed homogeneously.

13. The wearable fluid delivery device of claim 11, wherein the fourth coating is disposed in discrete regions of the second coating.

14. The wearable fluid delivery device of claim 11, wherein the second and fourth coatings overlap.

15. The wearable fluid delivery device of claim 11, wherein the second and fourth coatings are non-overlapping.

16. The wearable fluid delivery device of claim 11, wherein the fourth coating is disposed in a concentration gradient throughout the second coating.

17. The wearable fluid delivery device of claim 1, wherein the cannula comprises a third material mixed with the first material, the third material disposed in discrete regions of the cannula, the third material comprising at least one of the hydrophilic material, the anti-microbial material, the anti-inflammatory material, and the anti-thombogenic material, wherein the first, second, and third materials of the cannula each comprise different materials.

* * * * *